(12) United States Patent
Ahn

(10) Patent No.: US 12,251,323 B2
(45) Date of Patent: Mar. 18, 2025

(54) HEIGHT-EXPANDABLE SPINAL CAGE

(71) Applicants: GBS Commonwealth Co., Ltd., Seoul (KR); PMT Republic, Inc., Walnut, CA (US); Kyoung Gee Ahn, Seoul (KR)

(72) Inventor: Kyoung Gee Ahn, Seoul (KR)

(73) Assignees: Kyoung Gee Ahn, Seoul (KR); GBS Commonwealth Co., Ltd., Seoul (KR); PMT Republic, Inc., Walnut, CA (US)

( * ) Notice: Subject to any disclaimer, the term of this patent is extended or adjusted under 35 U.S.C. 154(b) by 382 days.

(21) Appl. No.: 17/871,864

(22) Filed: Jul. 22, 2022

(65) Prior Publication Data

US 2023/0060949 A1  Mar. 2, 2023

(30) Foreign Application Priority Data

Aug. 24, 2021 (KR) .......................... 10-2021-0111813

(51) Int. Cl.
 *A61F 2/44* (2006.01)
 *A61F 2/28* (2006.01)
 *A61F 2/46* (2006.01)
 *A61F 2/30* (2006.01)

(52) U.S. Cl.
 CPC ............... *A61F 2/447* (2013.01); *A61F 2/28* (2013.01); *A61F 2/4611* (2013.01); *A61F 2002/30383* (2013.01); *A61F 2002/30515* (2013.01); *A61F 2002/30617* (2013.01); *A61F 2002/30904* (2013.01); *A61F 2002/448* (2013.01); *A61F 2220/0025* (2013.01); *A61F 2250/0097* (2013.01); *A61F 2310/00359* (2013.01)

(58) Field of Classification Search
 None
 See application file for complete search history.

(56) References Cited

U.S. PATENT DOCUMENTS

| 8,062,375 B2 * | 11/2011 | Glerum ................... A61F 2/447 606/279 |
| 11,382,761 B2 * | 7/2022 | Altarac ................... A61F 2/442 |
| 2015/0342748 A1 * | 12/2015 | Baynham .............. A61F 2/4455 623/17.15 |
| 2015/0342749 A1 * | 12/2015 | Baynham ................ A61F 2/447 623/17.16 |
| 2016/0081814 A1 * | 3/2016 | Baynham ................ A61F 2/447 623/17.16 |

(Continued)

FOREIGN PATENT DOCUMENTS

| KR | 10-2020-0013889 A | 2/2020 |
| KR | 10-2021-0037997 A | 4/2021 |

(Continued)

*Primary Examiner* — Ellen C Hammond
(74) *Attorney, Agent, or Firm* — NKL Law; Jae Youn Kim

(57) ABSTRACT

Disclosed is a height-expandable spinal cage including an upper plate and a lower plate disposed to face each other, a frame disposed between the upper plate and the lower plate, the frame having a space formed therein, a block disposed between the upper plate and the lower plate and configured to be movable in a longitudinal direction inside the frame, and a driving bolt having one end thereof connected to the block to move the block. The height-expandable spinal cage is implanted into an affected area while occupying the minimum height thereof and to be expanded between vertebral bodies.

16 Claims, 20 Drawing Sheets

(56) References Cited

U.S. PATENT DOCUMENTS

| | | | |
|---|---|---|---|
| 2019/0021871 A1* | 1/2019 | Baynham | A61F 2/30771 |
| 2021/0315705 A1* | 10/2021 | Altarac | A61F 2/447 |
| 2022/0395383 A1* | 12/2022 | Jung | A61F 2/4601 |

FOREIGN PATENT DOCUMENTS

| | | |
|---|---|---|
| KR | 20210062904 A | 6/2021 |
| WO | 2017051416 A1 | 3/2017 |

* cited by examiner

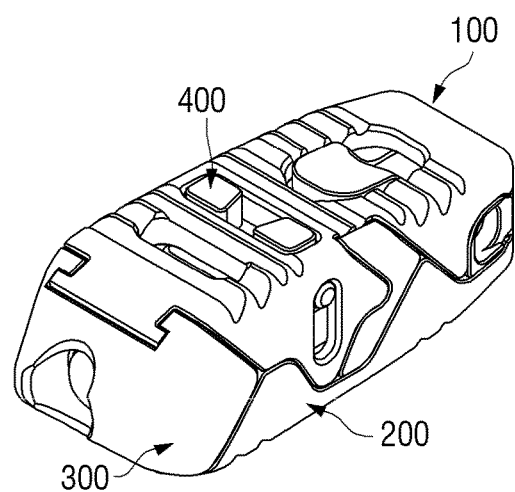
FIG. 1A
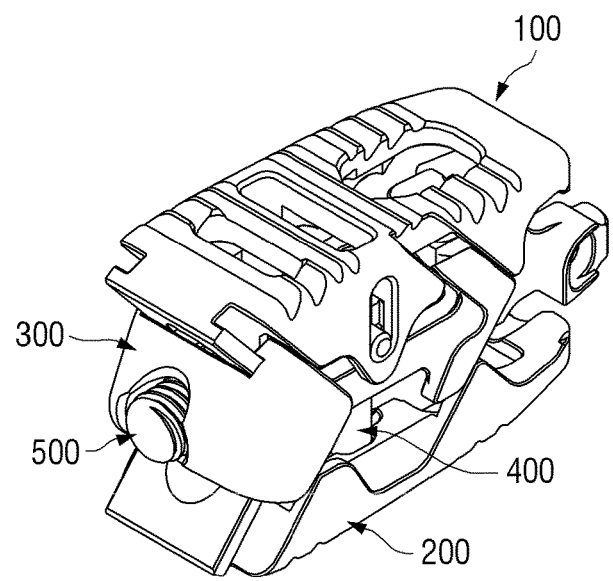
FIG. 1B
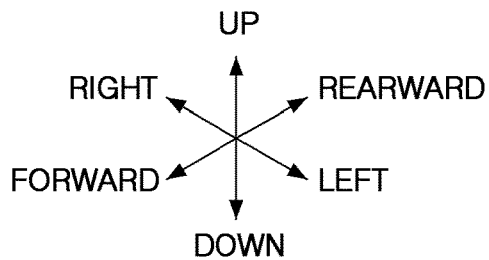

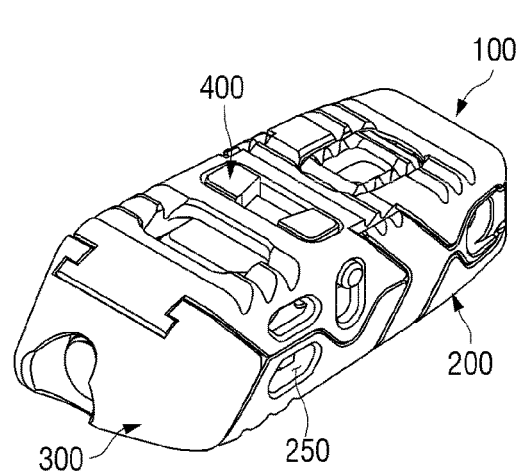
FIG. 20A
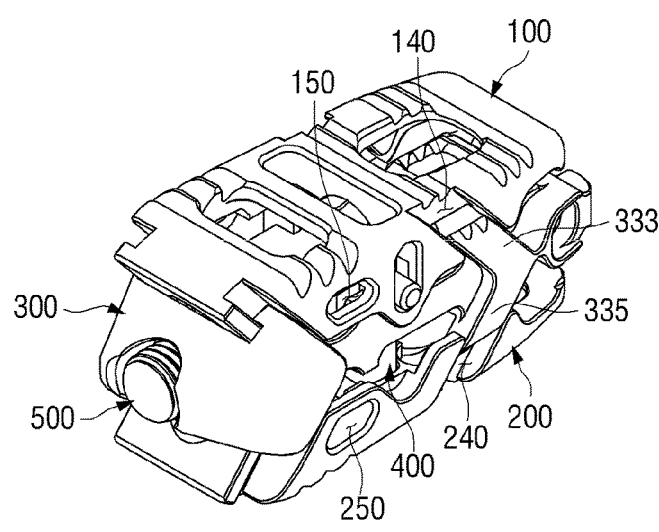
FIG. 20B
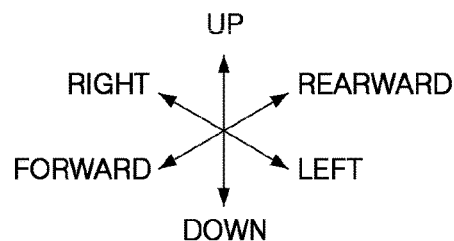

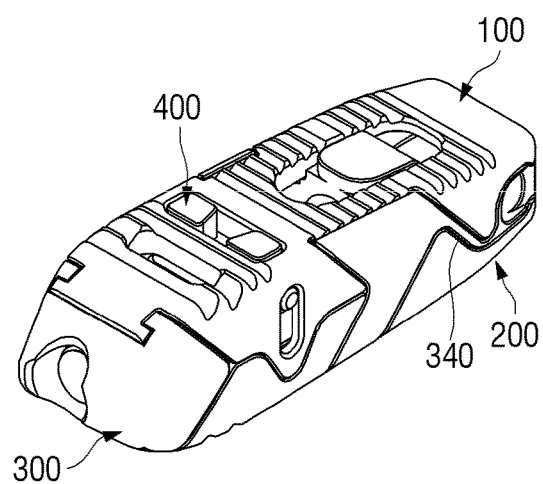
FIG. 21A
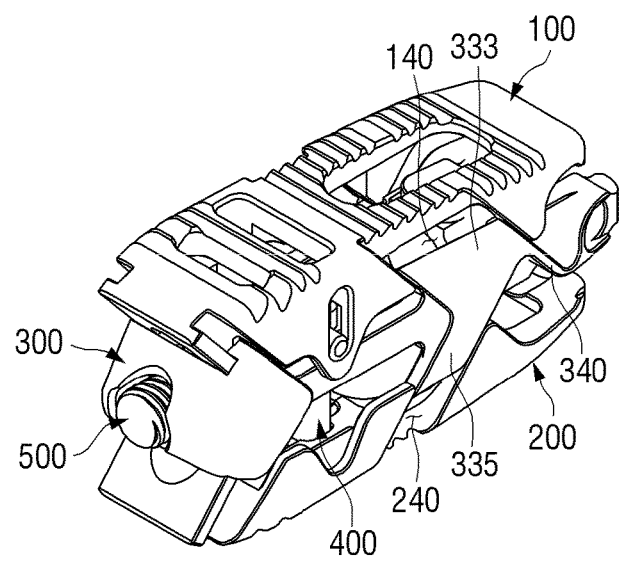
FIG. 21B
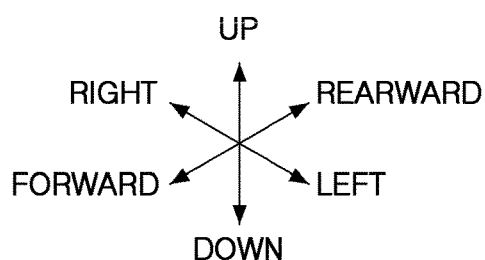

HEIGHT-EXPANDABLE SPINAL CAGE

BACKGROUND OF THE INVENTION

Field of the Invention

The present invention relates to a spinal cage, and more particularly to a height-expandable spinal cage configured to enable adjustment of the vertical distance between an upper plate and a lower plate by operating a driving bolt.

Description of the Related Art

The spine may have problems related to alignment thereof due to congenital abnormalities, degenerative abnormalities, or other reasons such as an accident, or may have structural problems such as a narrow gap between vertebral bodies. Representative spinal diseases include spinal deformity, spinal fracture, disc herniation, spinal stenosis, and facet joint hypertrophy. These spinal diseases require surgical treatment when symptoms thereof worsen and non-invasive treatment becomes ineffective.

Among surgical treatments, spinal fusion is surgery performed as follows. After an intervertebral disc affected by spinal disease is removed, a spinal cage is implanted between vertebral bodies to secure space for bone growth and bone fusion, and the gap between the vertebral bodies is increased to relive pain, thereby restoring the normal curvature of the spine and maintaining the stability of the spine.

In general, the spinal cage used in spinal fusion surgery has a hollow formed therein, and a bone chip is inserted into the hollow. As regeneration occurs around the bone chip, bone fusion occurs between the upper vertebral body and the lower vertebral body.

Various types of spinal cages have been developed for various treatment methods. For example, various efforts have been made to develop a spinal cage having a shape configured so as to be capable of being implanted in the human body to restore the biomechanical stability of the spine.

Since the spinal cage is required to maintain a predetermined distance between the vertebral bodies, the same has a solid structure made of a metal material such as titanium or a titanium alloy having sufficient mechanical strength to support the weight of a human.

However, since a spinal cage of the related art requires an implant path for implantation of the spinal cage into the affected area of a patient suffering from a spinal injury, bone or soft tissue needs to be removed. As a result, surgery may take a long time and side effects may occur due to removal of existing tissue.

The information disclosed in this Background of the Invention section is only for enhancement of understanding of the general background of the invention, and should not be taken as an acknowledgement or any form of suggestion that this information forms the related art already known to a person skilled in the art.

SUMMARY OF THE INVENTION

Therefore, the present invention has been made in view of the above problems, and it is an object of the present invention to provide a height-expandable spinal cage, configured to be implanted into an affected area while occupying a minimum height thereof and to be expanded between vertebral bodies.

It is another object of the present invention to provide a height-expandable spinal cage capable of being usefully used for minimally invasive surgery in a hospital.

The objects of the present invention are not limited to the above-mentioned objects, and other technical objects not mentioned herein will be clearly understood by those skilled in the art from the detailed description of the embodiments.

In accordance with the present invention, the above and other objects can be accomplished by the provision of a height-expandable spinal cage including an upper plate and a lower plate disposed to face each other, a frame disposed between the upper plate and the lower plate, the frame having a space formed therein, a block disposed between the upper plate and the lower plate and configured to be movable in a longitudinal direction inside the frame, and a driving bolt having one end thereof connected to the block to move the block, wherein a distance between the upper plate and the lower plate is increased or decreased when the block moves in the longitudinal direction.

The block may include a block body having a block hole formed in a center thereof, an upper protrusion formed to protrude from one surface of the block body toward the upper plate, and a lower protrusion formed to protrude from a remaining surface of the block body toward the lower plate.

The upper plate may have an upper penetration part formed therein, the upper penetration part allowing the upper protrusion to be inserted thereinto and accommodated therein, and the lower plate may have a lower penetration part formed therein, the lower penetration part allowing the lower protrusion to be inserted thereinto and accommodated therein, wherein the upper plate and the lower plate may be moved in a state in which the upper protrusion and the lower protrusion are accommodated in the upper penetration part and the lower penetration part, respectively, when the block moves in the longitudinal direction.

The block may further include a restraint groove formed in a side portion of the block body so as to be disposed between the upper protrusion and the lower protrusion, and a round-shaped rotation-inducing part disposed between the block hole in the block body and the restraint groove therein, wherein the restraint groove may have a connection part inserted thereinto and held therein, the connection part being formed at a side portion of the frame in the longitudinal direction.

The upper protrusion or the lower protrusion may have a fusion passage perforated therein.

The upper protrusion or the lower protrusion may have a restraint pin formed at a side portion thereof, the restraint pin protruding toward an outside of the frame, and the upper plate or the lower plate may have a long hole formed in a side portion thereof, the long hole being formed to be vertically elongated to correspond to a position of the restraint pin, wherein the restraint pin may be inserted into and accommodated in the long hole so as to be slidable therein.

The driving bolt may include a bolt body having male threads formed on an outer circumferential surface thereof, and a bolt head formed at an end of the bolt body, the bolt head having a diameter larger than a diameter of the bolt body.

The height-expandable spinal cage may further include a fixing groove formed between the bolt body and the bolt head, the fixing groove having a diameter smaller than the diameter of the bolt body, and a fixing ring inserted into and accommodated in the fixing groove, the fixing ring being formed in a 'C' shape with one side thereof open.

The bolt head may be accommodated in a block hole formed to penetrate through the block, wherein the block hole may further accommodate a fixing cap to come into contact with an end of the bolt head, the fixing cap being rotatable in the block hole.

The bolt head may have a bolt inclined surface formed at an end thereof, the bolt inclined surface being inclined at a predetermined inclination angle, and the fixing cap, contacting the end of the bolt head, may have a fixing inclined surface formed at an end thereof, the fixing inclined surface being formed to correspond to a shape of the bolt inclined surface, wherein the bolt inclined surface and the fixing inclined surface may be kept in close contact with each other when the fixing cap rotates.

The block hole may have a block end formed therein to allow a fixing end formed to protrude from a side portion of the fixing cap to be in contact with and supported by the block end, the block end being formed to protrude from an inside of the block hole.

The fixing cap may have a plurality of fixing rotation grooves formed in a side portion thereof so that the fixing cap is rotatable, the plurality of fixing rotation grooves being formed to be recessed into the side portion.

The frame may include a front part having a front hole formed therein, the front hole allowing a remaining end of the driving bolt to be inserted thereinto, a connection part extending in the longitudinal direction from one end of the front part, and a rear part coupled to one end of the connection part, wherein an internal space may be defined between the front part and the rear part in the longitudinal direction by the connection part.

The front part may have one surface contacting the upper plate, the one surface having a first front inclined rail formed thereon, and a remaining surface contacting the lower plate, the remaining surface having a second front inclined rail formed thereon, and the upper plate may have an upper inclined rail formed thereon to allow the first front inclined rail to be inserted thereinto and accommodated therein, and the lower plate may have a lower inclined rail formed thereon to allow the second front inclined rail to be inserted thereinto and accommodated therein.

The rear part may have a first frame protrusion formed on one side thereof, the first frame protrusion protruding toward the upper plate, and a second frame protrusion formed on the other side thereof, the second frame protrusion protruding toward the lower plate, and the upper plate may have an upper accommodation groove formed therein to allow the first frame protrusion to be accommodated in the upper accommodation groove, and the lower plate may have a lower accommodation groove formed therein to allow the second frame protrusion to be accommodated in the lower accommodation groove.

The first frame protrusion may have a first frame inclined surface formed on one surface thereof, the first frame inclined surface being inclined at a predetermined inclination angle, and the second frame protrusion may have a second frame inclined surface formed on one surface thereof, the second frame inclined surface being inclined at a predetermined inclination angle, and the upper plate may have an upper inclined surface formed in the upper accommodation groove thereof to correspond to the first frame inclined surface so that the first frame inclined surface contacts the upper inclined surface, and the lower plate may have a lower inclined surface formed in the lower accommodation groove thereof to correspond to the second frame inclined surface so that the second frame inclined surface contacts the lower inclined surface.

The rear part may have a frame penetration hole formed therein in the longitudinal direction, wherein the frame penetration hole may be connected to the internal space defined by the connection part.

The rear part may have a mechanism-coupling groove formed in a side portion thereof, the mechanism-coupling groove being formed to be recessed.

BRIEF DESCRIPTION OF THE DRAWINGS

The above and other objects, features and other advantages of the present invention will be more clearly understood from the following detailed description taken in conjunction with the accompanying drawings, in which:

FIGS. 1A-1B are views showing the overall appearance of a height-expandable spinal cage according to an embodiment of the present invention;

FIGS. 20A-20B are views showing the overall appearance of a height-expandable spinal cage according to another embodiment of the present invention; and FIGS. 21A-21B are views showing the overall appearance of a height-expandable spinal cage according to still another embodiment of the present invention.

DETAILED DESCRIPTION OF THE INVENTION

Hereinafter, the present invention will be described in detail with reference to the accompanying drawings so that those skilled in the art to which the present invention pertains can easily implement the present invention. However, the present invention may be implemented in various ways and is not limited to the embodiments described herein.

In order to clearly describe the present invention, parts irrelevant to the description are omitted. Wherever possible, the same reference numbers will be used throughout the drawings to refer to the same or like parts.

In addition, the terms or words used in the specification and claims should not be construed as being limited to conventional or dictionary meanings, but should be interpreted as having meanings and concepts consistent with the technical spirit of the present invention based on the principle that the inventor may appropriately define concepts of the terms in order to describe his or her invention in the best mode.

Figure 2:
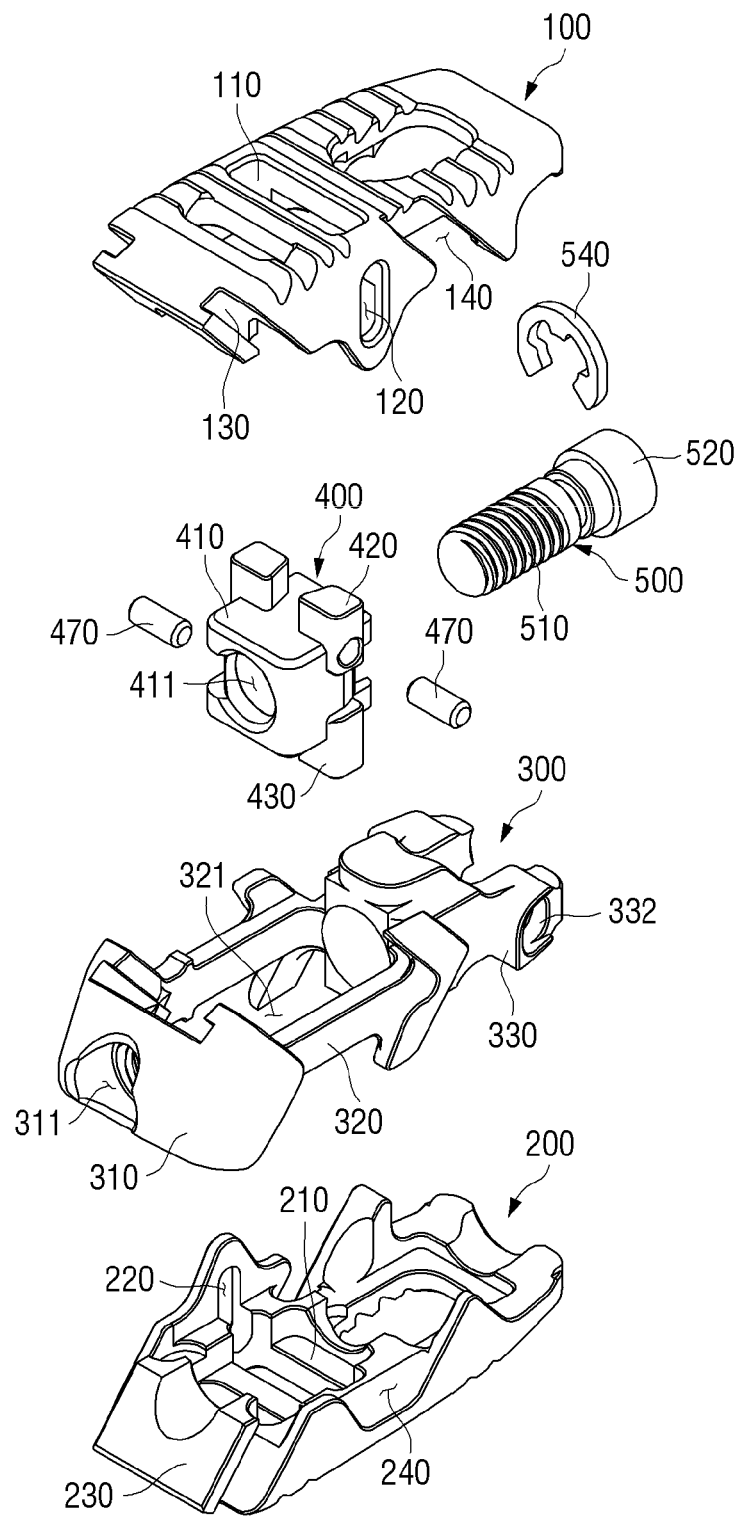
FIG. 2 is a view showing the exploded state of each component of the height-expandable spinal cage according to the embodiment of the present invention.

FIGS. 1A-1B are views showing the overall appearance of a height-expandable spinal cage according to an embodiment of the present invention, and FIG. 2 is a view showing the exploded state of each component of the height-expandable spinal cage according to the embodiment of the present invention.

FIG. 1A is a view showing the state before the height of the height-expandable spinal cage according to the embodiment of the present invention is increased, and FIG. 1B is a view showing the state after the height of the height-expandable spinal cage according to the embodiment of the present invention is increased.

As shown in FIGS. 1A-1B, the height-expandable spinal cage according to the present invention includes an upper plate 100, a lower plate 200, a frame 300, a block 400, and a driving bolt 500.

The upper plate 100 is disposed at the upper portion of the frame 300, and the lower plate 200 is disposed at the lower portion of the frame 300. A plurality of teeth are formed on the upper surface of the upper plate 100 and the lower surface of the lower plate 200. Here, the plurality of teeth dig into an upper vertebral body and a lower vertebral body so that the spinal cage has a constant fixing force between the vertebral bodies. The plurality of teeth allow the spinal cage to stably maintain the position thereof at the initial stage of spinal fusion procedures.

Each of the upper plate 100 and the lower plate 200 has a hollow formed therein. The hollow is filled with an autograft, allograft, or synthetic bone to accelerate bone growth.

In the embodiment, the upper plate 100, the lower plate 200, and the frame 300 are together formed in a long bullet shape in the forward-and-rearward direction, but are not limited thereto. The same may be formed in various shapes such as a flat shape, a curved shape, or a disk shape.

The frame 300 is disposed between the upper plate 100 and the lower plate 200. Specifically, the frame 300 includes a front part 310 having a front hole 311 formed therein, a connection part 320 extending in the longitudinal direction from the rear end of the front part 310, and a rear part 330 coupled to the rear end of the connection part 320. A pair of connection parts 320 is provided, and an internal space 321 is defined between the pair of connection parts 320 in the longitudinal direction.

The block 400 is disposed between the upper plate 100 and the lower plate 200, and may move in the longitudinal direction (the forward-and-rearward direction) in the internal space 321 defined by the pair of connection parts 320 of the frame 300.

The driving bolt 500 has the rear end thereof connected to the block 400, and may move in the forward-and-rearward direction to move the block 400. The driving bolt 500 is formed of a bolt body 510, having male threads 511 formed on the outer circumferential surface thereof, and a bolt head 520 formed at the end of the bolt body 510, the bolt head 520 having a diameter larger than that of the bolt body 510.

The front end of the bolt body 510 is rotatably inserted into the front hole 311 in the frame 300 to be movable forwards and rearwards, and the bolt head 520 is accommodated in the block 400 to pull the block 400 forwards and rearwards.

Normally, when the driving bolt 500 moves rearwards, the block 400 also moves rearwards, and the upper plate 100 and the lower plate 200 maintain a minimum height therebetween, as shown in FIG. 1A.

After the height-expandable spinal cage is implanted into an affected area and the driving bolt 500 is moved forwards, the block 400 also moves forwards, thereby moving the upper plate 100 and the lower plate 200 forwards. Accordingly, as shown in FIG. 1B, the distance between the upper plate 100 and the lower plate 200 is increased, thereby making it possible to increase the vertical distance between the vertebral bodies.

As described above, according to the present invention, the height-expandable spinal cage may be implanted into the affected area while occupying the minimum height thereof and may then be expanded between the vertebral bodies, thereby having an effect of being usefully used for minimally invasive surgery.

Figure 3:
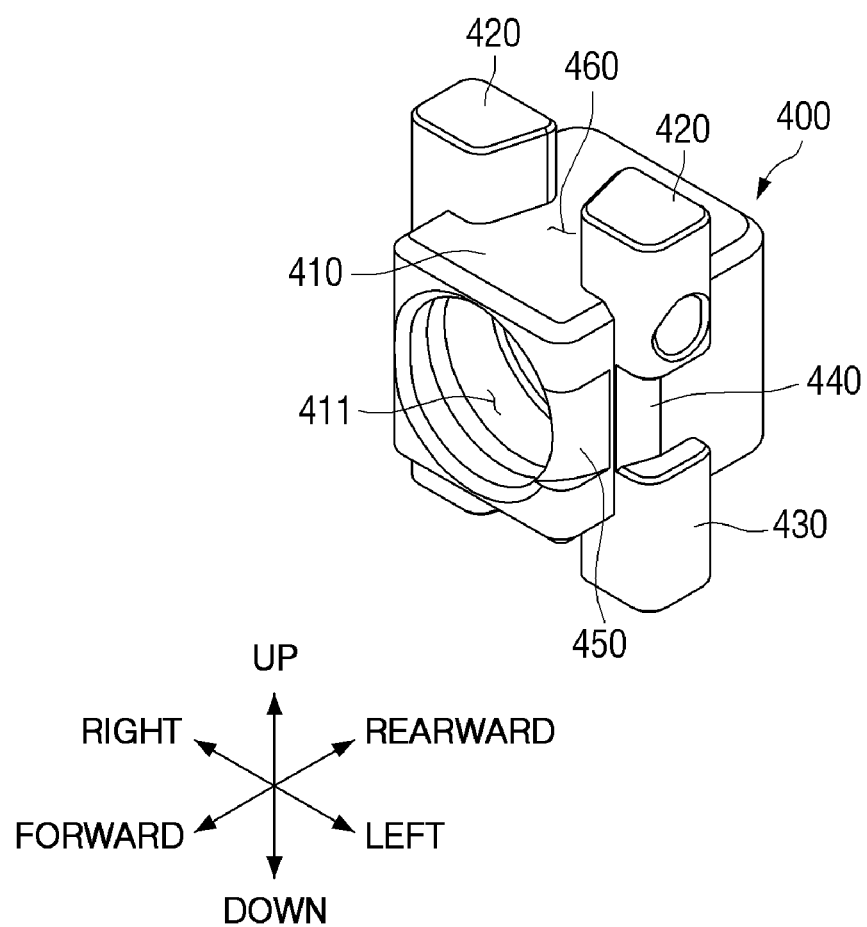
FIG. 3 is a view showing a block according to the embodiment of the present invention.
Figure 4:
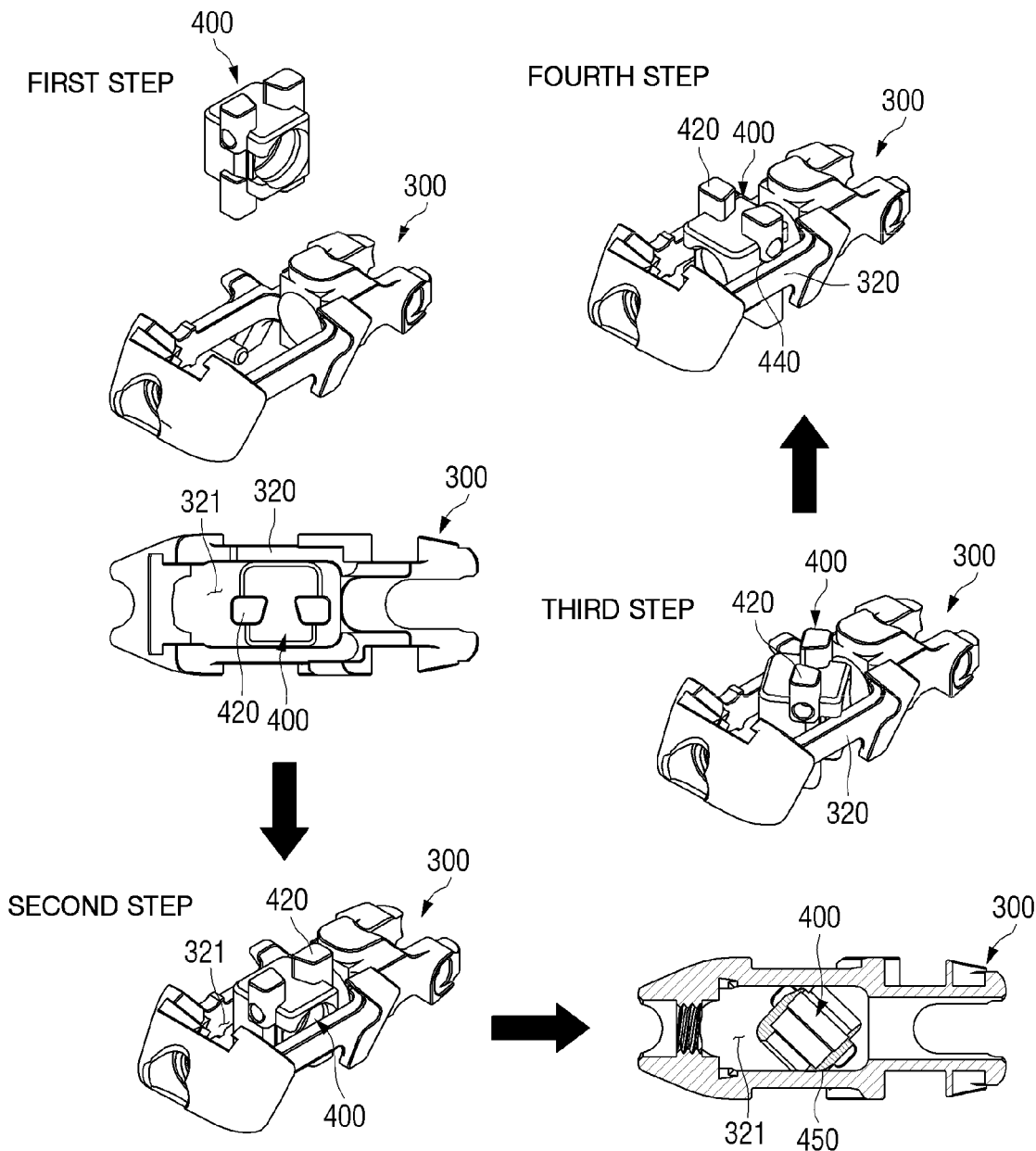
FIG. 4 is a view sequentially showing a process in which the block according to the embodiment of the present invention is inserted into a frame.
Figure 5:
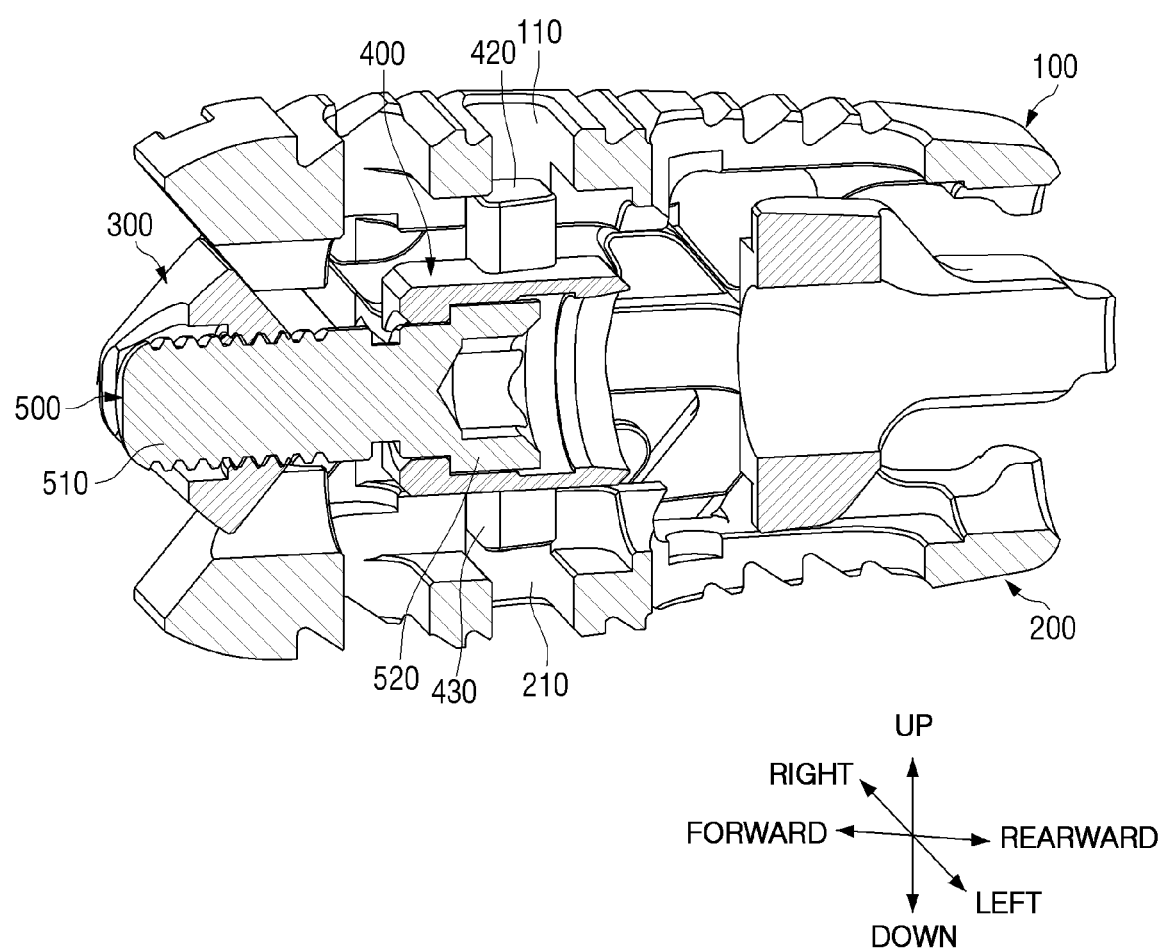
FIG. 5 is a view showing the state in which the height-expandable spinal cage according to the embodiment of the present invention is cut in the forward-and-rearward direction.
Figure 6:
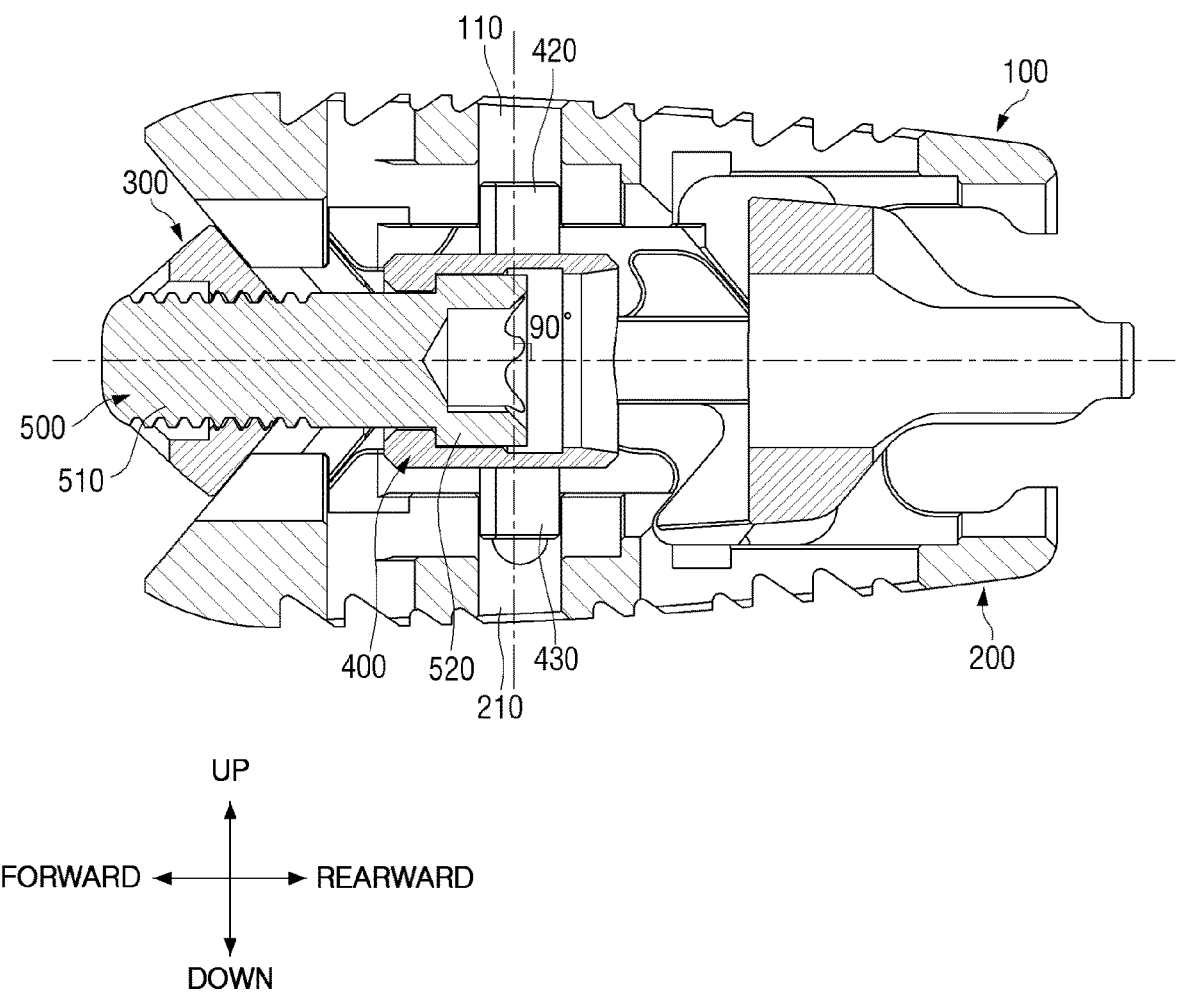
FIG. 6 is a cross-sectional view of the height-expandable spinal cage according to the embodiment of the present invention.
Figure 7A:
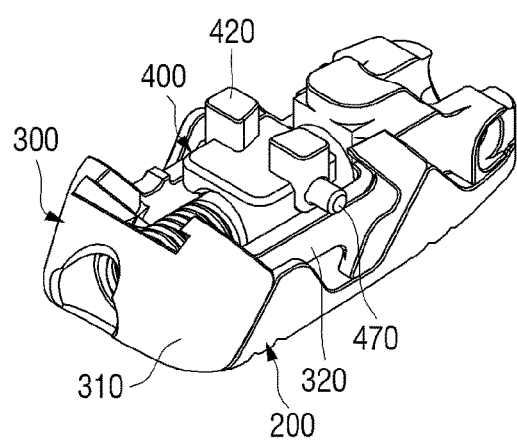
FIGS. 7A-7B are views showing the state in which a restraint pin is inserted into the block according to the embodiment of the present invention.
Figure 7B:
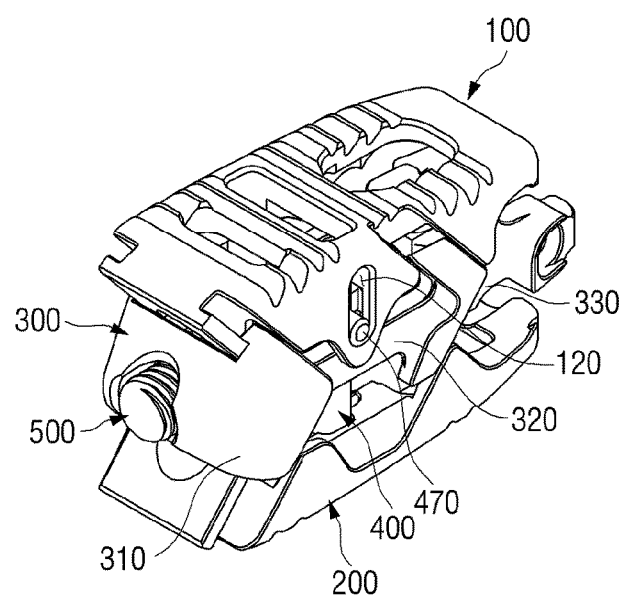

FIG. 3 is a view showing the block according to the embodiment of the present invention, FIG. 4 is a view sequentially showing a process in which the block according to the embodiment of the present invention is inserted into the frame, FIG. 5 is a view showing the state in which the height-expandable spinal cage according to the embodiment of the present invention is cut in the forward-and-rearward direction, FIG. 6 is a cross-sectional view of the height-expandable spinal cage according to the embodiment of the present invention, and FIGS. 7A-7B are views showing the state in which a restraint pin is inserted into the block according to the embodiment of the present invention.

As shown in FIG. 3, the block 400 includes a block body 410 having a block hole 411 formed in the center thereof, an upper protrusion 420 protruding from one surface of the block body 410 toward the upper plate 100, and a lower protrusion 430 protruding from the other surface of the block body 410 toward the lower plate 200.

The block body 410 is formed in a hexahedral shape overall, and the block hole 411 is formed through the center of the block body 410 in the forward-and-rearward direction. The bolt head 520 of the driving bolt 500 is accommodated in the block hole 411. A pair of upper protrusions 420 is formed on the upper surface of the block body 410, and a pair of lower protrusions 430 is formed on the lower surface of the block body 410.

A restraint groove 440 is formed at the side portion of the block body 410. The restraint groove 440 is disposed between the upper protrusion 420 and the lower protrusion 430, and has the connection part 320 of the frame 300 inserted thereinto and held therein. In the embodiment, a pair of restraint grooves 440 is provided.

As shown in FIG. 4, the width between the pair of restraint grooves 440 formed in the respective side portions of the block body 410 is the same as the width of the internal space 321 between the pair of connection parts 320, and the outermost widths of the upper protrusion 420 and the lower protrusion 430 are greater than the width of the internal space 321 between the pair of connection parts 320. Accordingly, the block 400 may move in the forward-and-rearward direction without being separated from the internal space 321 between the pair of connection parts 320.

A fusion passage 460 is perforated between the pair of upper protrusions 420 or between the pair of lower protrusions 430. The fusion passage 460 provides a passage to allow autogenous bone, allograft bone, or synthetic bone to pass therethrough. The fusion passage 460 may be formed in the upper surface of the block body 410, the lower surface thereof, or both the upper and lower surfaces thereof.

A round-shaped rotation-inducing part 450 is disposed between the block hole 411 and the restraint groove 440 in the block body 410. The rotation-inducing part 450 is formed to be recessed into the side surface of the block body 410, and connects the block hole 411 to the restraint groove 440.

As shown in FIG. 4, the block 400 is formed to have a length in the leftward-and-rightward direction greater than a length in the forward-and-rearward direction due to the upper protrusion 420 or the lower protrusion 430.

Accordingly, in order to position the block 400 in the internal space 321 between the connection parts 320 of the frame 300, first, the upper protrusion 420 and the lower protrusion 430 of the block 400 are disposed so as to be oriented in the longitudinal direction (the forward-and-rearward direction) (step 1).

Then, the block 400 is inserted into the internal space 321 in the frame 300 so that the block 400 is disposed between the connection parts 320 (step 2). The block 400 is rotated so that the upper protrusion 420 and the lower protrusion 430 are disposed orthogonal to the longitudinal direction (the leftward-and-rightward direction) (step 3).

In this case, the rotation-inducing part 450 is in contact with the inner surface of the connection part 320 so that the connection part 320 is located in the restraint groove 440 between the upper protrusion 420 and the lower protrusion 430. When the block 400 is completely rotated by 90 degrees, the connection part 320 of the frame 300 is inserted into and held in the restraint groove 440.

As shown in FIGS. 5 and 6, the upper plate 100 has an upper penetration part 110 formed therein and configured to allow the upper protrusion 420 to be inserted thereinto and accommodated therein, and the lower plate 200 has a lower penetration part 210 formed therein and configured to allow the lower protrusion 430 to be inserted thereinto and accommodated therein.

When the driving bolt 500 rotates and moves forwards and rearwards, the block 400 coupled to the rear end of the driving bolt 500 also moves forwards and rearwards. In this case, since the upper protrusion 420 and the lower protrusion 430 are inserted into and accommodated in the upper penetration part 110 and the lower penetration part 210, respectively, the upper plate 100 and the lower plate 200 may be pulled forwards and rearwards together with the block 400.

The upper penetration part 110 and the lower penetration part 210 are disposed to be orthogonal to the longitudinal direction (the forward-and-rearward direction) of the frame 300, and the upper protrusion 420 and the lower protrusion 430 are also disposed to be orthogonal to the longitudinal direction of the frame 300.

FIG. 7A is a view showing the state in which a restraint pin is coupled to the block according to the embodiment of the present invention, and FIG. 7B is a view showing the state in which the restraint pin according to the embodiment of the present invention is inserted into a long hole.

As shown in the drawings, a restraint pin 470 is formed at the side portion of the upper protrusion 420 or the lower protrusion 430 so as to protrude toward the outside of the frame 300. A long hole 120 or 220, which is elongated in the vertical direction, is formed in a side portion of the upper plate 100 or the lower plate 200 so as to be aligned with the position of the restraint pin 470.

The restraint pin 470 is slidably inserted into and accommodated in the long hole 120 or 220. Accordingly, the distance that the upper plate 100 or the lower plate 200 is capable of moving vertically may be limited. When the restraint pin 470 is located at the lowermost end of the long hole 120 in the upper plate 100, the upper plate 100 has the maximum height, that is, the upper plate 100 is raised as far as possible.

Figure 8:
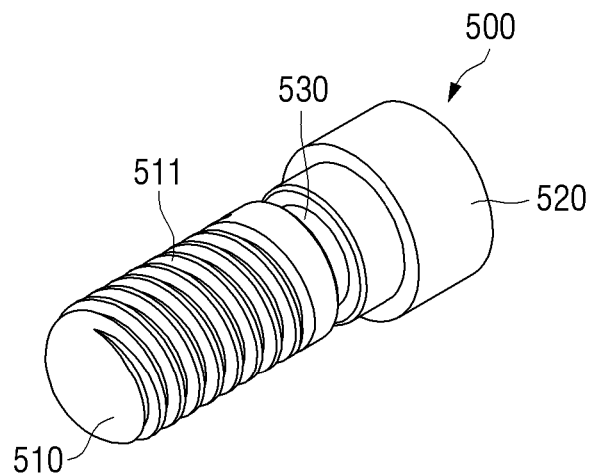
FIG. 8 is a view showing a driving bolt according to the embodiment of the present invention.
Figure 9:
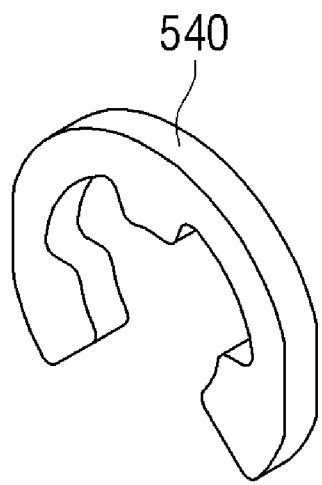
FIG. 9 is a view showing a fixing ring according to the embodiment of the present invention.
Figure 10:
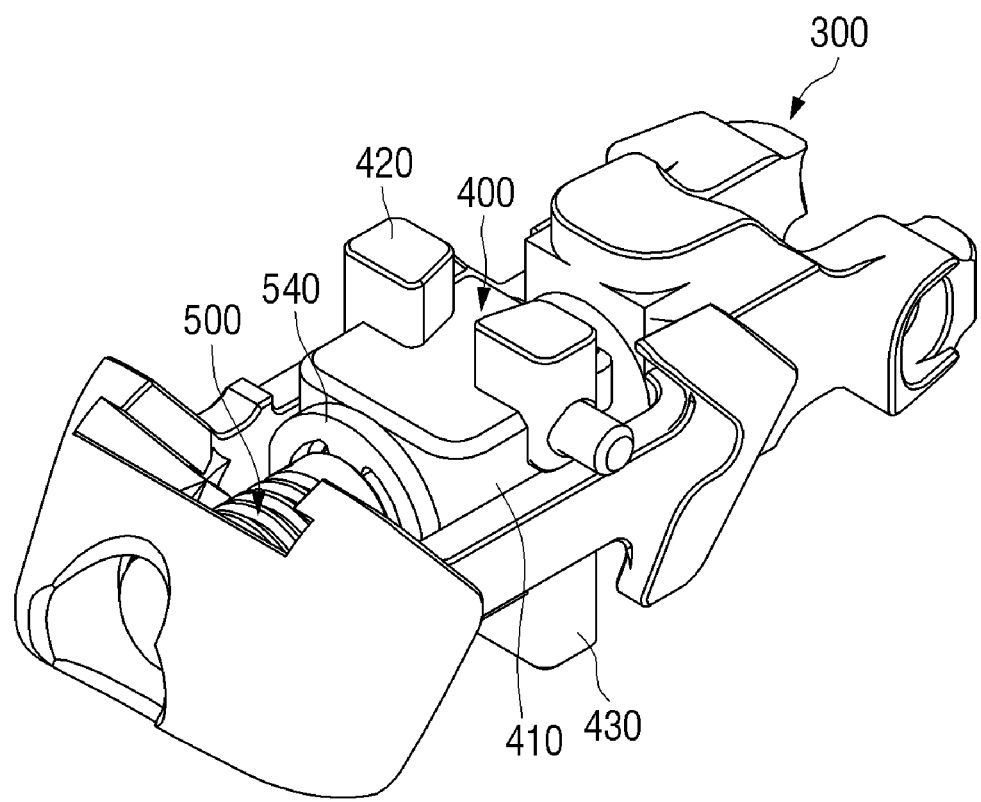
FIG. 10 is a view showing the state in which the fixing ring is coupled to the driving bolt according to the embodiment of the present invention.
Figure 11:
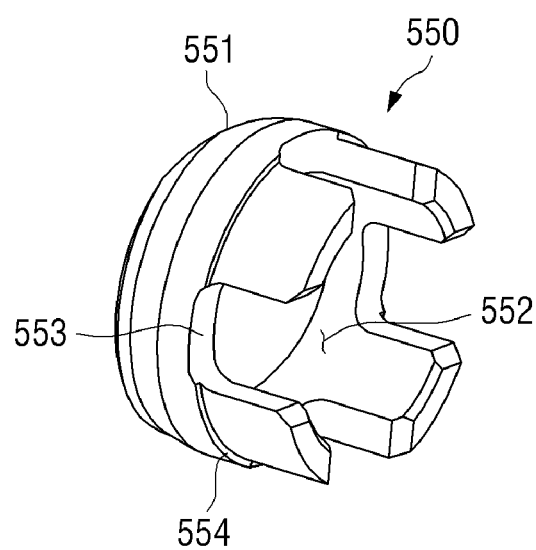
FIG. 11 is a view showing a fixing cap according to the embodiment of the present invention.
Figure 12A:
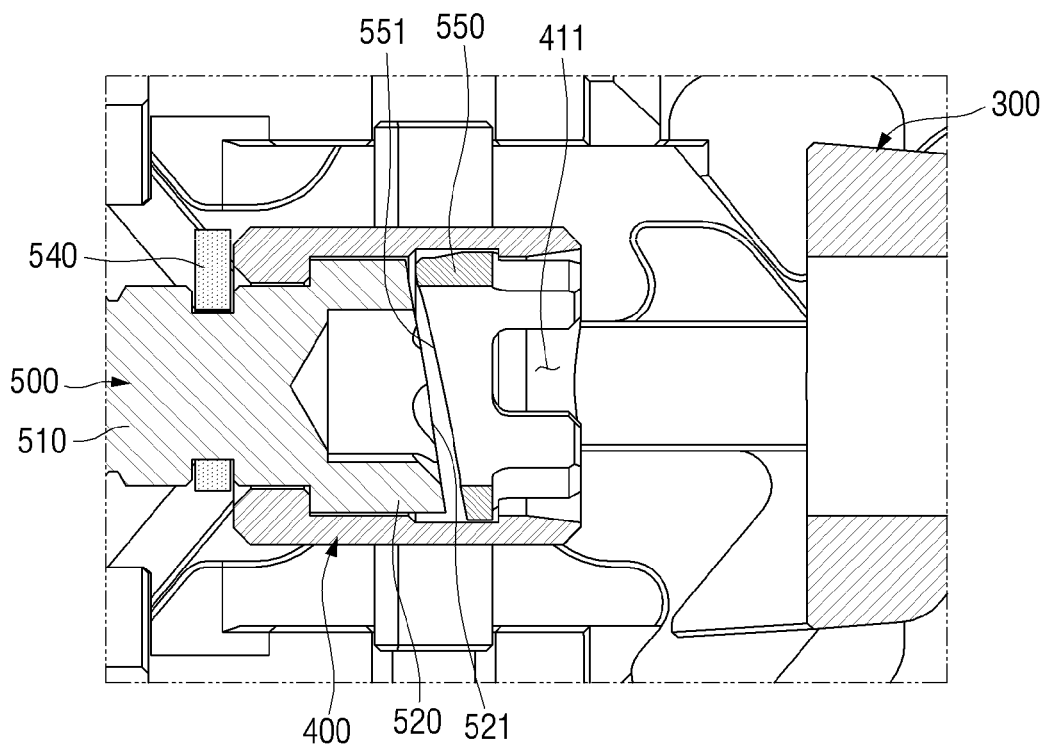
FIGS. 12A-12B are partial cross-sectional views showing the state in which the fixing cap according to the embodiment of the present invention is inserted into the block.
Figure 12B:
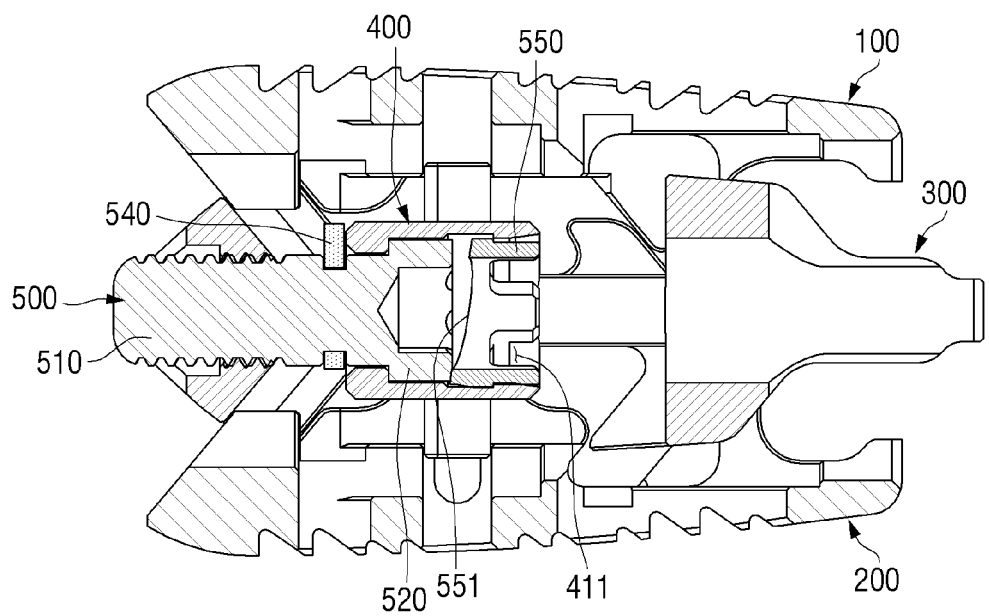
Figure 13:
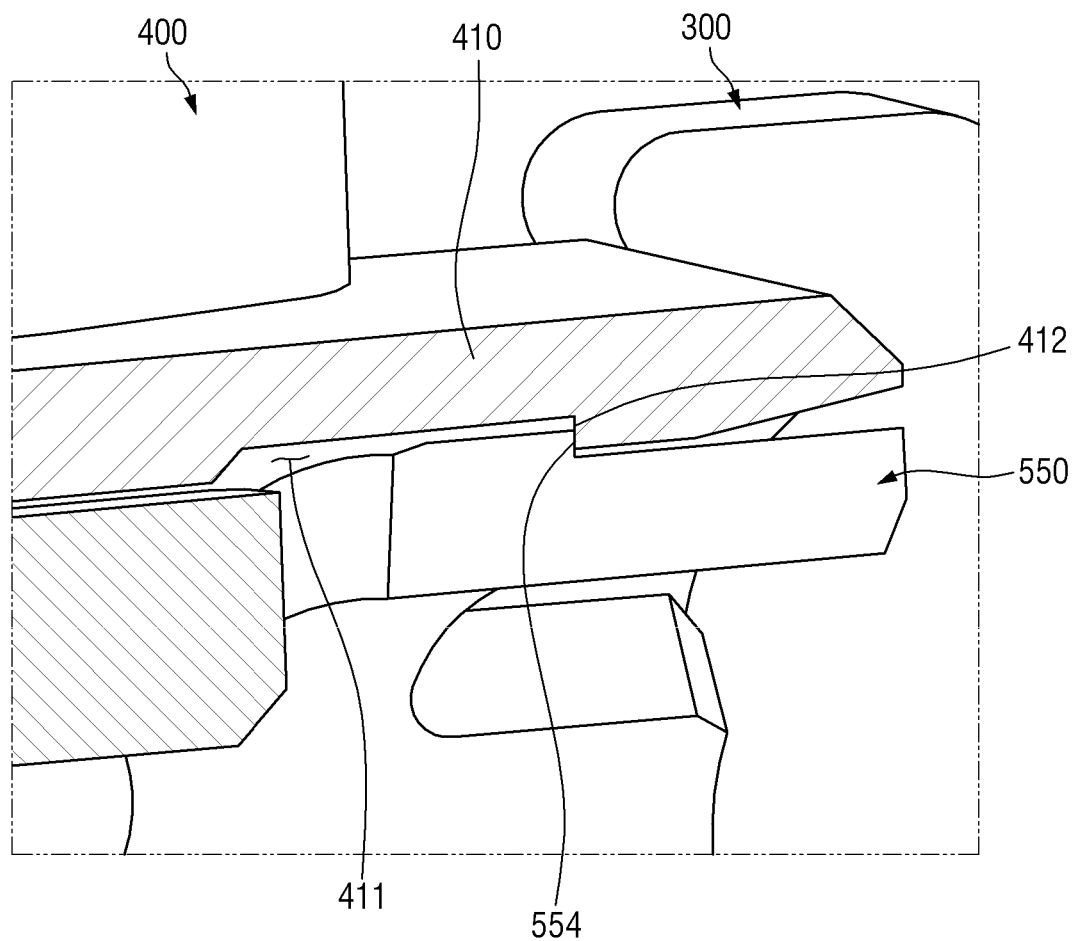
FIG. 13 is a partial cross-sectional view showing the state in which a fixing end of the fixing cap according to the embodiment of the present invention is in contact with and supported by a block end.

FIG. 8 is a view showing the driving bolt according to the embodiment of the present invention, FIG. 9 is a view showing a fixing ring according to the embodiment of the present invention, FIG. 10 is a view showing the state in which the fixing ring is coupled to the driving bolt according to the embodiment of the present invention, FIG. 11 is a view showing a fixing cap according to the embodiment of the present invention, FIGS. 12A-12B are partial cross-sectional views showing the state in which the fixing cap according to the embodiment of the present invention is inserted into the block, and FIG. 13 is a partial cross-sectional view showing the state in which a fixing end of the fixing cap according to the embodiment of the present invention is in contact with and supported by a block end.

As shown in the drawings, the driving bolt 500 includes the bolt body 510, the bolt head 520, and a fixing groove 530. The bolt body 510 is formed in a cylindrical shape, and has the male threads 511 formed on the outer circumferential surface thereof. The bolt head 520 is coupled to the rear end of the bolt body 510, and has a diameter larger than that of the bolt body 510. The fixing groove 530 is formed between the bolt body 510 and the bolt head 520, and has a diameter smaller than that of the bolt body 510.

As shown in FIGS. 9 and 10, a fixing ring 540 is coupled to the fixing groove 530. The fixing ring 540 is formed in a 'C' shape with one side thereof open, and may be inserted into and accommodated in the fixing groove 530, or may be separated from the fixing groove 530.

When the fixing ring 540 is coupled to the fixing groove 530, the rear surface of the fixing ring 540 is in contact with the front surface of the block 400. The bolt head 520, having a diameter larger than that of the bolt body 510, is accommodated in the block 400, and the fixing ring 540 is in contact with the front surface of the block 400. Accordingly, the driving bolt 500 is rotatably coupled to the block 400 to pull the block 400.

As shown in FIGS. 11 and 12A-12B, a fixing cap 550 to come into contact with the rear end of the bolt head 520 may be further accommodated in the block hole 411 in the block 400 so as to be rotatable therein.

FIG. 12A is a partial cross-sectional view showing the state in which the fixing cap according to the embodiment of the present invention is in contact with the rear end of the bolt head, and FIG. 12B is a partial cross-sectional view showing the state in which the fixing cap according to the embodiment of the present invention rotates to be in close contact with the rear end of the bolt head.

A bolt inclined surface 521 inclined at a predetermined inclination angle is formed at the rear end of the bolt head 520. A fixing inclined surface 551 is formed at the front end of the fixing cap 550 to come into contact with the rear end of the bolt head 520, the fixing inclined surface 551 being formed so as to correspond to the shape of the bolt inclined surface 521.

When the vertical distance between the upper plate 100 and the lower plate 200 is set by operating the driving bolt 500 as shown in FIG. 12A, the fixing inclined surface 551 presses the bolt inclined surface 521 by rotating the fixing cap 550 inserted into the block hole 411, and the fixing inclined surface 551 and the bolt inclined surface 521 are kept in close contact with each other, as shown in FIG. 12B. Accordingly, the driving bolt 500 is firmly fixed without loosening.

In this case, the fixing cap 550 includes a fixing hole 552 opening in the longitudinal direction (the forward-and-rearward direction) of the frame 300, and a plurality of fixing rotation grooves 553 are recessed into a side portion of the fixing cap 550 so as to hold and rotate the fixing cap 550. In the embodiment, the number of fixing rotation grooves 553 is four, but the number thereof is not limited thereto.

A fixing end 554 is formed to protrude in the shape of a ring from the side portion of the fixing cap 550. As shown in FIG. 13, the fixing end 554 is in contact with and supported by a block end 412 formed to protrude from the inside of the block hole 411. Accordingly, the fixing cap 550 is prevented from becoming separated from the block hole 411.

Figure 14:
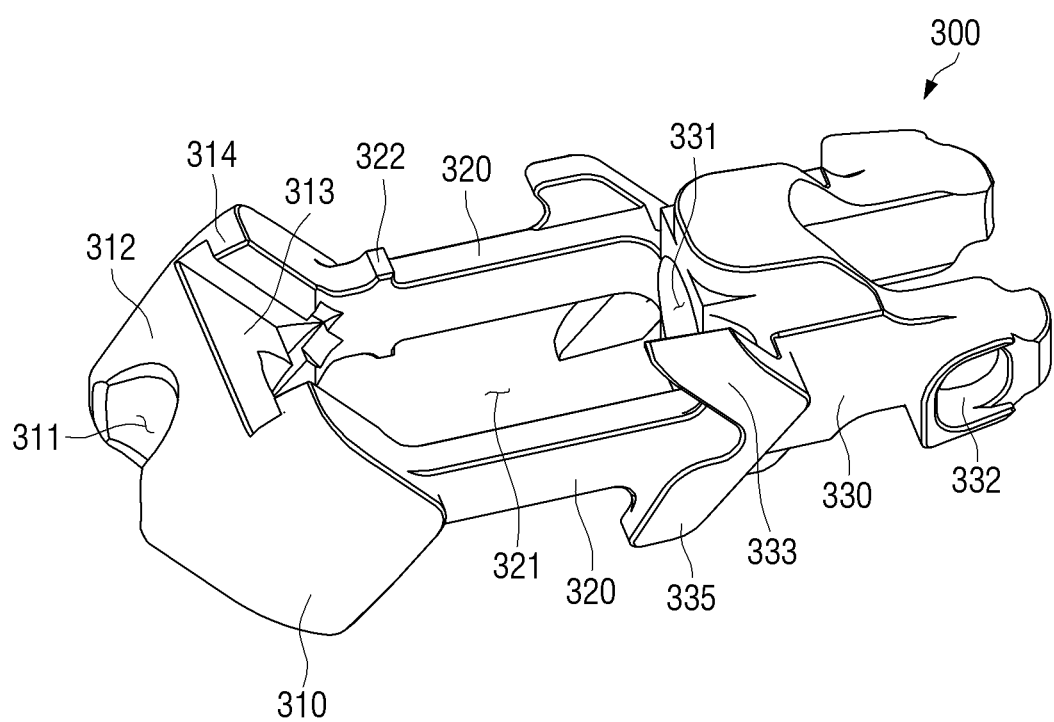
FIG. 14 is a view showing a frame according to the embodiment of the present invention.
Figure 15:
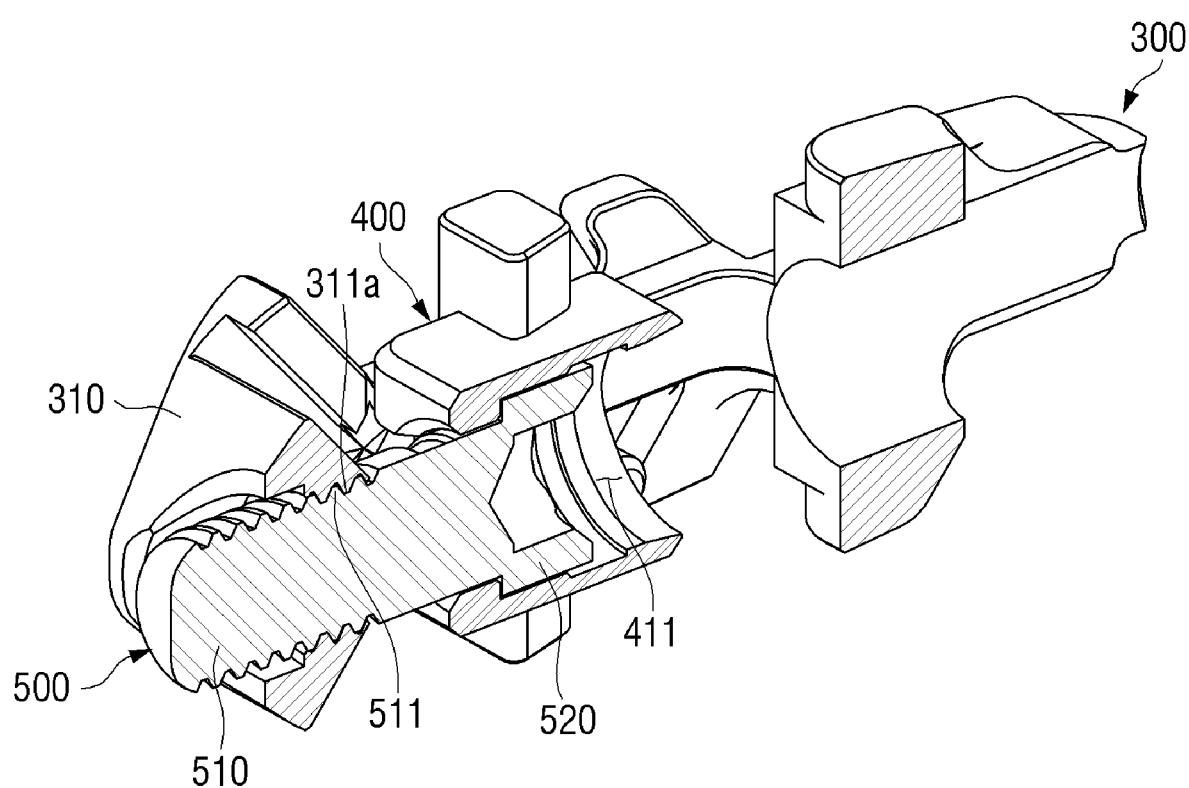
FIG. 15 is a partial cross-sectional view showing the state in which the driving bolt is inserted into a front part of the frame according to the embodiment of the present invention.
Figure 16A:
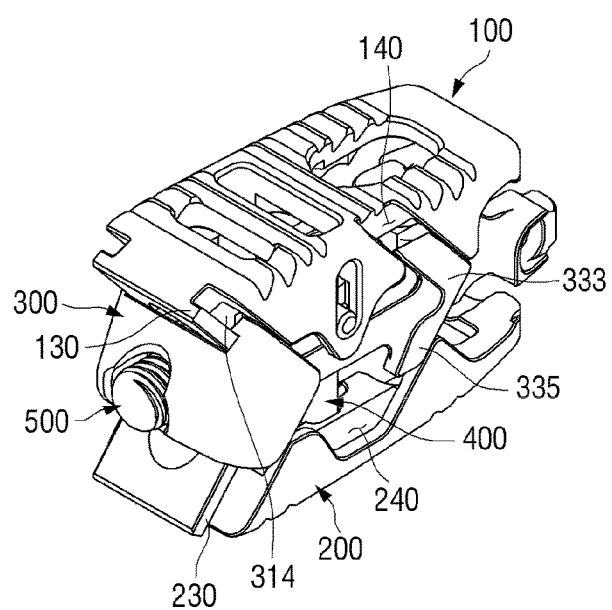
FIGS. 16A-16B are views showing the state in which the vertical distance between an upper plate and a lower plate according to the embodiment of the present invention is increased.
Figure 16B:
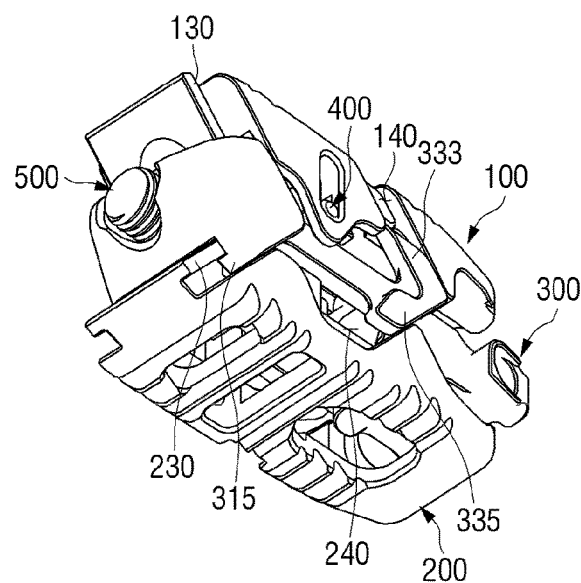
Figure 17:
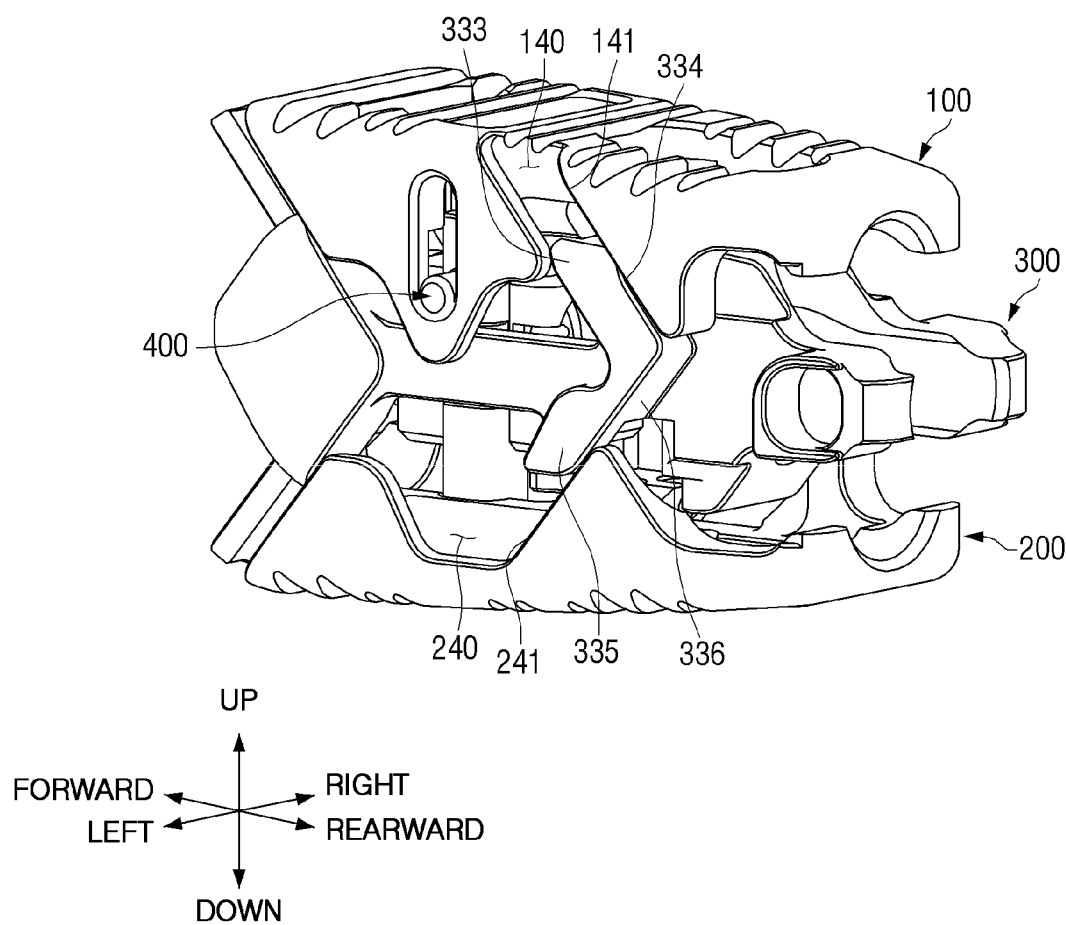
FIG. 17 is a view showing the state in which the vertical distance between the upper plate and the lower plate according to the embodiment of the present invention is increased, seen from the rear.
Figure 18:
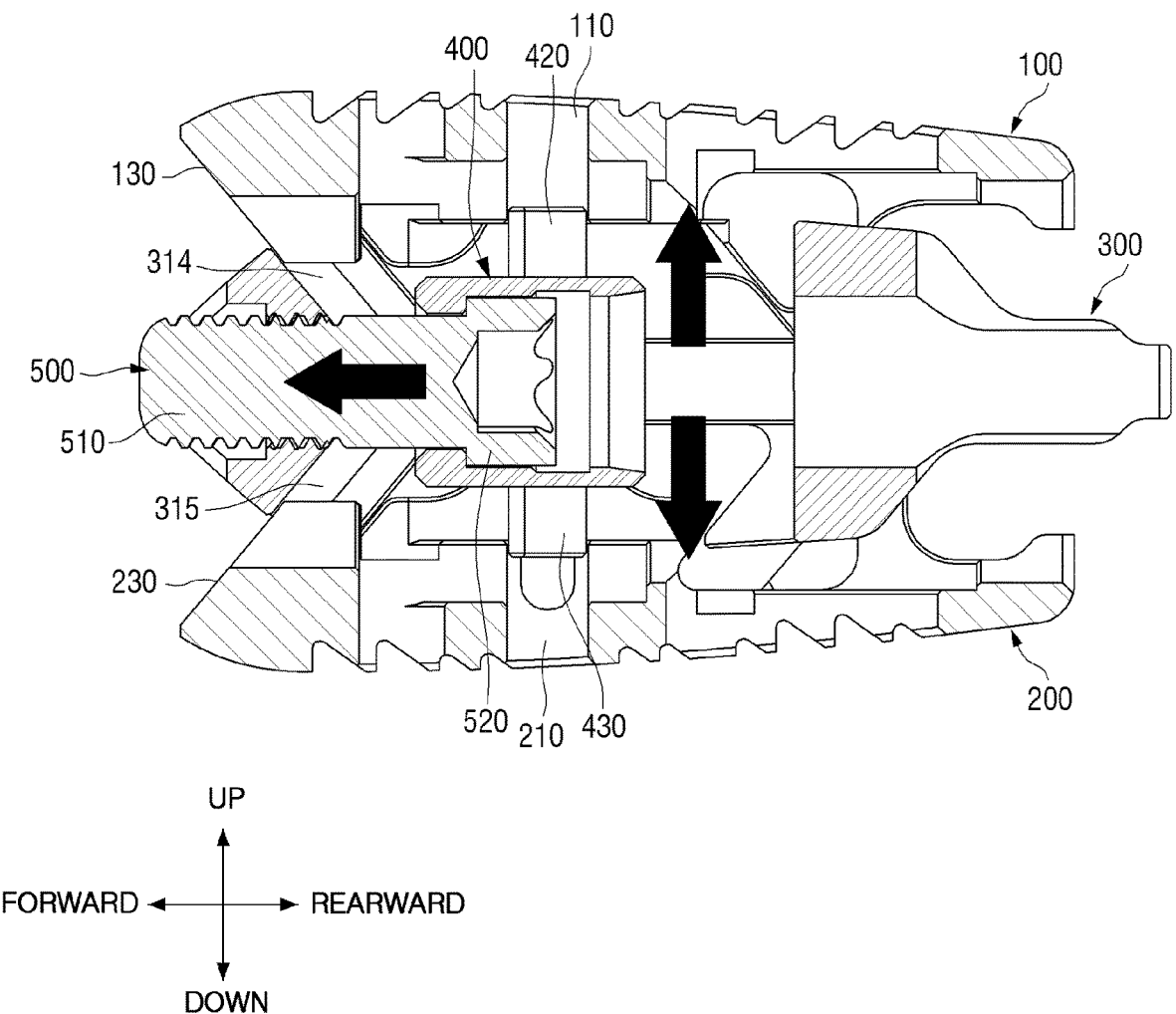
FIG. 18 is a cross-sectional view showing the state in which the vertical distance between the upper plate and the lower plate according to the embodiment of the present invention is increased.
Figure 19:
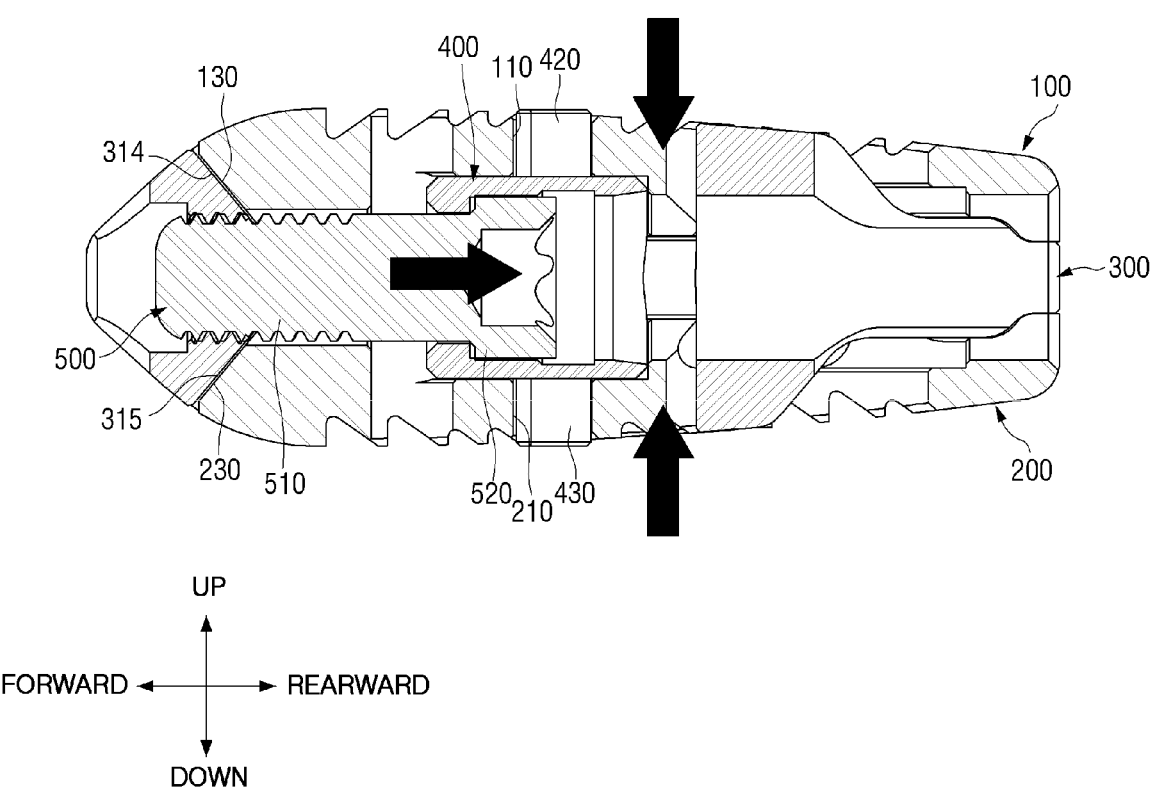
FIG. 19 is a cross-sectional view showing the state in which the vertical distance between the upper plate and the lower plate according to the embodiment of the present invention is decreased.

FIG. 14 is a view showing the frame according to the embodiment of the present invention, FIG. 15 is a partial cross-sectional view showing the state in which the driving bolt is inserted into a front part of the frame according to the embodiment of the present invention, FIG. 16 are views showing the state in which the vertical distance between the upper plate and the lower plate according to the embodiment of the present invention is increased, FIG. 17 is a view showing the state in which the vertical distance between the upper plate and the lower plate according to the embodiment of the present invention is increased, seen from the rear, FIG. 18 is a cross-sectional view showing the state in which the vertical distance between the upper plate and the lower plate according to the embodiment of the present invention is increased, and FIG. 19 is a cross-sectional view showing the state in which the vertical distance between the upper plate and the lower plate according to the embodiment of the present invention is decreased.

FIG. 16A is a view showing the state in which the vertical distance between the upper plate and the lower plate according to the embodiment of the present invention is increased, seen from above, and FIG. 16B is a view showing the state in which the vertical distance between the upper plate and the lower plate according to the embodiment of the present invention is increased, seen from below.

As shown in the drawings, the frame 300 includes the front part 310, the connection part 320, and the rear part 330.

A front inclined surface 312 oriented at a predetermined angle relative to the center of the front part 310 is formed on the front surface of the front part 310, and a rear inclined surface 313 oriented at a predetermined angle relative to the center thereof is also formed on the rear surface of the front part 310.

As shown in FIG. 15, the front hole 311 is formed in the center of the front part 310 in the longitudinal direction (the forward-and-rearward direction), and female threads 311a are formed on the inner surface of the front hole 311 to be engaged with the male threads 511 of the driving bolt 500.

When the driving bolt 500 is rotated, the male threads 511 of the driving bolt 500 are engaged with the female threads 311a of the front hole 311. Accordingly, the driving bolt 500 may move forwards or rearwards with respect to the frame 300.

The connection part 320 extends rearwards from the rear end of the front part 310. In the embodiment, a pair of connection parts 320 is provided, but the number thereof is not limited thereto. The internal space 321 is defined between the pair of connection parts 320, and the block 400 and the driving bolt 500 may be accommodated in the internal space 321.

A stopper 322 may be formed to protrude from one side of the connection part 320, and the upper protrusion 420 or the lower protrusion 430 of the block 400 may be in contact with and supported by the stopper 322.

The rear part 330 is coupled to the rear end of the connection part 320. A frame penetration hole 331 is formed in the center of the rear part 330 in the longitudinal direction (the forward-and-rearward direction), and the frame penetration hole 331 is connected to the internal space 32.

A mechanism-coupling groove 332 is formed to be recessed into a side portion of the rear part 330. The mechanism-coupling groove 332 allows the frame 300 to be coupled to a predetermined mechanism. In the embodiment, each of the mechanism-coupling grooves 332 is formed in a corresponding one of opposite sides of the rear part 330, but the present invention is not limited thereto.

As shown in FIGS. 16A-16B, a first front inclined rail 314 is formed on the rear inclined surface 313 of the front part 310 that is in contact with the upper plate 100, and a second front inclined rail 315 is formed on the rear inclined surface 313 of the front part 310 that is in contact with the lower plate 200.

An upper inclined rail 130 is formed on the upper plate 100 so that the first front inclined rail 314 may be inserted into and accommodated in the upper plate 100. A lower inclined rail 230 is formed on the lower plate 200 so that the second front inclined rail 315 may be inserted into and accommodated in the lower plate 200.

When the driving bolt 500 is moved forwards by rotating the driving bolt 500, the block 400 coupled to the driving bolt 500 also moves forwards. When the block 400 moves forwards, the upper plate 100 and the lower plate 200 also move forwards.

When the upper plate 100 and the lower plate 200 move forwards as shown in FIG. 18, the upper inclined rail 130 moves forwards and upwards in the state of being accommodated in the first front inclined rail 314, and the lower inclined rail 230 moves forwards and downwards in the state of being accommodated in the second front inclined rail 315. Accordingly, the distance between the upper plate 100 and the lower plate 200 is increased, thereby making it possible to increase the vertical distance between the upper plate 100 and the lower plate 200.

On the other hand, when the driving bolt 500 is moved rearwards by rotating the driving bolt 500, the block 400 coupled to the driving bolt 500 also moves rearwards. When the block 400 moves rearwards, the upper plate 100 and the lower plate 200 also move rearwards.

When the upper plate 100 and the lower plate 200 move rearwards as shown in FIG. 19, the upper inclined rail 130 moves rearwards and downwards in the state of being accommodated in the first front inclined rail 314, and the lower inclined rail 230 moves rearwards and upwards in the state of being accommodated in the second front inclined rail 315. Accordingly, the distance between the upper plate 100 and the lower plate 200 is decreased, thereby making it possible to decrease the vertical distance therebetween.

As shown in FIG. 17, a first frame protrusion 333 protruding toward the upper plate 100 is formed on the upper portion of the rear part 330, and a second frame protrusion 335 protruding toward the lower plate 200 is formed on the lower portion of the rear part 330.

An upper accommodation groove 140 is formed in the upper plate 100 to allow the first frame protrusion 333 to be accommodated in the upper accommodation groove 140, and a lower accommodation groove 240 is formed in the lower plate 200 to allow the second frame protrusion 335 to be accommodated in the lower accommodation groove 240.

When the vertical distance between the upper plate 100 and the lower plate 200 is increased, the first frame protrusion 333 and the second frame protrusion 335 are separated from the upper accommodation groove 140 and the lower accommodation groove 240, respectively. On the other hand, when the vertical distance between the upper plate 100 and the lower plate 200 is decreased, the first frame protrusion 333 and the second frame protrusion 335 are accommodated in the upper accommodation groove 140 and the lower accommodation groove 240, respectively.

A first frame inclined surface 334 inclined at a predetermined inclination angle is formed on the rear surface of the first frame protrusion 333, and a second frame inclined surface 336 inclined at a predetermined inclination angle is formed on the rear surface of the second frame protrusion 335.

An upper inclined surface 141 is formed in the upper accommodation groove 140 of the upper plate 100 so as to correspond to the shape of the first frame inclined surface 334. Accordingly, the upper inclined surface 141 may contact the first frame inclined surface 334. Further, a lower inclined surface 241 is formed in the lower accommodation groove 240 of the lower plate 200 so as to correspond to the shape of the second frame inclined surface 336. Accordingly, the lower inclined surface 241 may contact the second frame inclined surface 336.

When the upper plate 100 and the lower plate 200 move forwards, the upper inclined surface 141 moves forwards and upwards while riding over the first frame inclined surface 334, and the lower inclined surface 241 moves forwards and downwards while riding over the second frame inclined surface 336. As a result, the distance between the upper plate 100 and the lower plate 200 is increased, thereby making it possible to increase the vertical distance between the upper plate 100 and the lower plate 200.

On the other hand, when the upper plate 100 and the lower plate 200 move rearwards, the upper inclined surface 141 moves rearwards and downwards while riding down the first frame inclined surface 334, and the lower inclined surface 241 moves rearwards and upwards while riding down the second frame inclined surface 336. As a result, the distance between the upper plate 100 and the lower plate 200 is decreased, thereby making it possible to decrease the vertical distance therebetween.

FIG. 20 are views showing the overall appearance of a height-expandable spinal cage according to another embodiment of the present invention, and FIGS. 21A-21B are views showing the overall appearance of a height-expandable spinal cage according to still another embodiment of the present invention.

FIG. 20A is a view showing the state before the height of the height-expandable spinal cage according to another embodiment of the present invention is increased, and FIG. 20B is a view showing the state after the height of the height-expandable spinal cage according to another embodiment of the present invention is increased. FIG. 21A is a view showing the state before the height of the height-expandable spinal cage according to still another embodiment of the present invention is increased, and FIG. 21B is a view showing the state after the height of the height-expandable spinal cage according to still another embodiment of the present invention is increased.

As shown in FIGS. 20A-20B, the height-expandable spinal cage according to another embodiment of the present invention includes the upper plate 100, the lower plate 200, the frame 300, the block 400, and the driving bolt 500, as in the case of the height-expandable spinal cage according to the embodiment of the present invention shown in FIGS. 1A-1B.

In the height-expandable spinal cage according to another embodiment of the present invention, both the upper portion of the upper accommodation groove 140 and the lower portion of the lower accommodation groove 240 are open, and as such, the upper end of the first frame protrusion 333 and the lower end of the second frame protrusion 335 are exposed to the outside. On the other hand, the height-expandable spinal cage according to the embodiment of the present invention shown in FIGS. 1A-1B is different in that the lower portion of the lower accommodation groove 240 is closed, and as such, the lower end of the second frame protrusion 335 is not exposed to the outside.

As shown in FIGS. 21A-21B, the height-expandable spinal cage according to still another embodiment of the present invention also includes the upper plate 100, the lower plate 200, the frame 300, the block 400, and the driving bolt 500, as in the case of the height-expandable spinal cage according to the embodiment of the present invention shown in FIG. 1.

In the height-expandable spinal cage according to still another embodiment of the present invention, both the upper portion of the upper accommodation groove 140 and the lower portion of the lower accommodation groove 240 are also open, and as such, the upper end of the first frame protrusion 333 and the lower end of the second frame protrusion 335 are exposed to the outside, as in the case of the height-expandable spinal cage according to another embodiment of the present invention shown in FIGS. 20A-20B.

Meanwhile, the first frame protrusion 333 of the height-expandable spinal cage according to still another embodiment of the present invention is further connected to the mechanism-coupling groove 332 through an additional connection member 340. On the other hand, the height-expandable spinal cage according to the embodiment of the present invention shown in FIGS. 1A-1B is different in that there is no additional connection member between the first frame protrusion 333 and the mechanism-coupling groove 332 other than the rear part 330.

As is apparent from the above description, a height-expandable spinal cage of the present invention having the above-described configuration has an effect of making it possible to increase or decrease the vertical distance between an upper plate and a lower plate by moving a block forwards or rearwards in the longitudinal direction inside a frame.

In other words, according to the present invention, the height-expandable spinal cage may be implanted into an affected area of a patient suffering from a spinal injury in the state in which the height is reduced to the minimum height thereof, and the height of the height-expandable spinal cage may be expanded in the affected area, thereby having an effect of being usefully used for minimally invasive surgery.

Although preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A height-expandable spinal cage comprising:
    an upper plate and a lower plate disposed to face each other;
    a frame disposed between the upper plate and the lower plate, the frame having a space formed therein;
    a block disposed between the upper plate and the lower plate and movable in a longitudinal direction of the frame inside the frame; and
    a driving bolt having one end thereof connected to the block to move the block,
    wherein a distance between the upper plate and the lower plate is increased or decreased when the block moves in the longitudinal direction,
    wherein the frame comprises:
    a front part having a front hole formed therein, the front hole allowing another end of the driving bolt to be inserted thereinto;
    a connection part extending in the longitudinal direction from one end of the front part; and
    a rear part coupled to one end of the connection part,
    wherein an internal space is defined between the front part and the rear part in the longitudinal direction by the connection part,
    the front part has one surface contacting the upper plate, the one surface having a first front inclined rail formed thereon, and another surface contacting the lower plate, the another surface having a second front inclined rail formed thereon, and
    the upper plate has an upper inclined rail formed thereon to allow the first front inclined rail to be inserted thereinto and accommodated therein, and the lower plate has a lower inclined rail formed thereon to allow the second front inclined rail to be inserted thereinto and accommodated therein.

2. The height-expandable spinal cage according to claim 1, wherein the block comprises:
    a block body having a block hole formed in a center thereof;
    an upper protrusion formed to protrude from one surface of the block body toward the upper plate; and
    a lower protrusion formed to protrude from another surface of the block body toward the lower plate.

3. The height-expandable spinal cage according to claim 2, wherein:
    the upper plate has an upper penetration part formed therein, the upper penetration part allowing the upper protrusion to be inserted thereinto and accommodated therein, and
    the lower plate has a lower penetration part formed therein, the lower penetration part allowing the lower protrusion to be inserted thereinto and accommodated therein,
    wherein the upper plate and the lower plate are moved in a state in which the upper protrusion and the lower protrusion are accommodated in the upper penetration part and the lower penetration part, respectively, when the block moves in the longitudinal direction.

4. The height-expandable spinal cage according to claim 2, wherein the block further comprises:
    a restraint groove formed in a side portion of the block body so as to be disposed between the upper protrusion and the lower protrusion; and
    a round-shaped rotation-inducing part disposed between the block hole in the block body and the restraint groove therein,
    wherein the restraint groove has a connection part inserted thereinto and held therein, the connection part being formed at a side portion of the frame in the longitudinal direction.

5. The height-expandable spinal cage according to claim 2, wherein the upper protrusion or the lower protrusion has a fusion passage perforated therein.

6. The height-expandable spinal cage according to claim 2, wherein:
    the upper protrusion or the lower protrusion has a restraint pin formed at a side portion thereof, the restraint pin protruding toward an outside of the frame, and
    the upper plate or the lower plate has a long hole formed in a side portion thereof, the long hole being formed to be vertically elongated to correspond to a position of the restraint pin,
    wherein the restraint pin is inserted into and accommodated in the long hole so as to be slidable therein.

7. The height-expandable spinal cage according to claim 1, wherein the driving bolt comprises:
    a bolt body having male threads formed on an outer circumferential surface thereof; and
    a bolt head formed at an end of the bolt body, the bolt head having a diameter larger than a diameter of the bolt body.

8. The height-expandable spinal cage according to claim 7, further comprising:
    a fixing groove formed between the bolt body and the bolt head, the fixing groove having a diameter smaller than the diameter of the bolt body; and
    a fixing ring inserted into and accommodated in the fixing groove, the fixing ring being formed in a 'C' shape with one side thereof open.

9. The height-expandable spinal cage according to claim 7, wherein the bolt head is accommodated in a block hole formed to penetrate through the block,
    wherein the block hole further accommodates a fixing cap to come into contact with an end of the bolt head, the fixing cap being rotatable in the block hole.

10. The height-expandable spinal cage according to claim 9, wherein:
    the bolt head has a bolt inclined surface formed at an end thereof, the bolt inclined surface being inclined at a predetermined inclination angle, and the fixing cap, contacting the end of the bolt head, has a fixing inclined surface formed at an end thereof, the fixing inclined surface being formed to correspond to a shape of the bolt inclined surface, wherein the bolt inclined surface and the fixing inclined surface are kept in contact with each other when the fixing cap rotates.

11. The height-expandable spinal cage according to claim 9, wherein the block hole has a block end formed therein to allow a fixing end formed to protrude from a side portion of the fixing cap to be in contact with and supported by the block end, the block end being formed to protrude from an inside of the block hole.

12. The height-expandable spinal cage according to claim 9, wherein the fixing cap has a plurality of fixing rotation grooves formed in a side portion thereof so that the fixing cap is rotatable, the plurality of fixing rotation grooves being formed to be recessed into the side portion.

13. The height-expandable spinal cage according to claim 1, wherein:

the rear part has a first frame protrusion formed on one side thereof, the first frame protrusion protruding toward the upper plate, and a second frame protrusion formed on another side thereof, the second frame protrusion protruding toward the lower plate, and the upper plate has an upper accommodation groove formed therein to allow the first frame protrusion to be accommodated in the upper accommodation groove, and the lower plate has a lower accommodation groove formed therein to allow the second frame protrusion to be accommodated in the lower accommodation groove.

14. The height-expandable spinal cage according to claim 13, wherein:

the first frame protrusion has a first frame inclined surface formed on one surface thereof, the first frame inclined surface being inclined at a predetermined inclination angle, and the second frame protrusion has a second frame inclined surface formed on one surface thereof, the second frame inclined surface being inclined at another predetermined inclination angle, and the upper plate has an upper inclined surface formed in the upper accommodation groove thereof to correspond to the first frame inclined surface so that the first frame inclined surface contacts the upper inclined surface, and the lower plate has a lower inclined surface formed in the lower accommodation groove thereof to correspond to the second frame inclined surface so that the second frame inclined surface contacts the lower inclined surface.

15. The height-expandable spinal cage according to claim 1, wherein the rear part has a frame penetration hole formed therein in the longitudinal direction, wherein the frame penetration hole is connected to the internal space defined by the connection part.

16. The height-expandable spinal cage according to claim 1, wherein the rear part has a mechanism-coupling groove formed in a side portion thereof, the mechanism-coupling groove being formed to be recessed.

* * * * *